(12) United States Patent
Goh et al.

(10) Patent No.: US 8,415,503 B2
(45) Date of Patent: Apr. 9, 2013

(54) METHOD FOR PREPARATION OF 1,1-DIAMINO-2,2-DINITROETHYLENE

(75) Inventors: Eun Mee Goh, Yuseong-gu (KR); Jin Seuk Kim, Yuseong-gu (KR)

(73) Assignee: Agency for Defense Development, Yuseong-Gu, Daejeon (KR)

( * ) Notice: Subject to any disclaimer, the term of this patent is extended or adjusted under 35 U.S.C. 154(b) by 95 days.

(21) Appl. No.: 13/176,949

(22) Filed: Jul. 6, 2011

(65) Prior Publication Data

US 2012/0178968 A1 Jul. 12, 2012

(30) Foreign Application Priority Data

Jul. 7, 2010 (KR) .................. 10-2010-0065552

(51) Int. Cl.
*C07C 209/62* (2006.01)
*C07C 209/50* (2006.01)

(52) U.S. Cl. ........................ 564/487; 564/486

(58) Field of Classification Search .................. 564/486, 564/487

See application file for complete search history.

(56) References Cited

PUBLICATIONS

Nikolai V. Latypov and Jan Bergman; Tetrahedron vol. 54; Synthesis and Reaction of 1,1-Diamino-2,2-dinitroethylene; May 11, 1998; p. 11525-11536.
Astrat'Ev, Dashko, Mershin, Stepanov, Urazgil'Deev; Russian Journal of Organic Chemistry vol. 37 No. 5; Some Specific Features of Acid Nitration of 2-Substituted 4, 6-Dihydroxypyrimidines; Nucleophilic Cleavage of the Nitration Products; May 15, 2000; p. 729-733.
Nikolaj V. Latypov, Martin Johansson and Erik Holmgren; Organic Process Research and Development 2007, 11,; On the Synthesis of 1,1-Diamino-2,2-dinitroethene (FOX—7) by Nitration of 4, 6-Dihydroxy-2-methylpryimidine; Dec. 24, 2006; p. 56-59.

*Primary Examiner* — Brian J Davis
(74) *Attorney, Agent, or Firm* — Kenneth E. Horton; Kirton McConkie

(57) ABSTRACT

Disclosed is a method for preparation of 1,1-diamino-2,2-dinitroethylene (DADNE) through the hydrolysis of 4,6-dihydroxy-5,5-dinitro-2-(dinitromethylene)-2,5-dihydropyrimidine (DHDNDP) obtained by the nitration of 4,6-dihydroxy-2-methylpyrimidine (DHMP), which can avoid eruption or sudden frothing of a reaction solution on a lab scale and even a large scale preparation as well as reduce the reaction time.

1 Claim, 3 Drawing Sheets

METHOD FOR PREPARATION OF 1,1-DIAMINO-2,2-DINITROETHYLENE

FIELD OF THE INVENTION

The present invention relates to a method for preparation of 1,1-diamino-2,2-dinitroethylene (DADNE), specifically a method for preparation of DADNE through the hydrolysis of 4,6-dihydroxy-5,5-dinitro-2-(dinitromethylene)-2,5-dihydropyrimidine (DHDNDP) obtained by the nitration of 4,6-dihydroxy-2-methylpyrimidine (DHMP). According to the present method, it is possible to avoid an eruption or sudden frothing of a reaction solution on a small or large scale as well as reduce the reaction time by controlling reaction conditions.

BACKGROUND OF THE INVENTION 1,1-diamino-2,2-dinitroethylene (DADNE) that is a type of insensitive explosives, is generally synthesized by hydrolyzing 4,6-dihydroxy-5,5-dinitro-2-(dinitromethylene)-2,5-dihydropyrimidine (DHDNDP) obtained from the nitration of 4,6-dihydroxy-2-methylpyrimidine (DHMP). In the hydrolysis reaction, DHDNDP is decomposed in water to give the final product, DADNE, together with the same mole number of dinitromethane and carbon dioxide as side products. Along with DADNE that is a type of explosives, the side product dinitromethane is also an explosive material which may involve explosion and decomposition at an ambient temperature and thus likely to cause problems in this hydrolysis reaction.

A hydrolysis process of DHDNDP which has been most widely used is a method proposed by N. V. Latypove et al., *Organic Process Research & Development*, Vol. 11, No. 1, 2007, pp. 56-59. The above method is comprised of dissolving DHDNDP into water, vigorously stirring the reaction solution overnight while maintaining the inner temperature at 20° C. or less and filtering the resulted solution. The method uses a reactor having the volume of 90 L, and other experiments or methods which used a larger reactor than said volume has not been reported so far.

However, the Latypove's method has a problem that an eruption or sudden frothing of the reactants occurs usually in about 6 hours after the beginning of the reaction, due to instability of dinitromethane generated during the hydrolysis reaction. In the meantime, this eruption or frothing was not reported in the above publication, and it is because a small amount of reactants relative to the volume of the reactor was used at low temperature. Therefore, although such eruption or frothing did not reported in said publication, the above method still has a potential problem of an eruption or frothing, due to the presence of dinitromethane together with the explosive DADNE when conducted on a large scale.

SUMMARY OF THE INVENTION

The present invention which has been designed to solve the problems of the prior arts, as described above, is to provide a method for preparation of DADNE through the hydrolysis of DHDNDP obtained by the nitration of DHMP, which is characterized by adjusting the hydrolysis reaction temperature to an increased temperature. According to the present method, it is possible to avoid an eruption or sudden frothing of a reaction solution even when carried out on a large scale as well as reduce the reaction time.

DETAILED DESCRIPTION OF THE INVENTION

The method for preparing DADNE according to the present invention is characterized by comprising the following steps:

(1) preparing 4,6-dihydroxy-5,5-dinitro-2-(dinitromethylene)-2,5-dihydropyrimidine (DHDNDP) through the nitration of 4,6-dihydroxy-2-methylpyrimidine (DHMP);

(2) dissolving DHDNDP prepared in the above step (1) into water in a reactor at an inner temperature of the reactor of 30-60° C., and maintaining the resulted solution at the same temperature for 1.5-2.0 hours; and (3) lowering the inner temperature of the reactor to 20-25° C., then filtering and washing the resulted product to obtain 1,1-diamino-2,2-dinitroethylene.

The present method for preparing DADNE is schematically represented in the following reaction scheme.

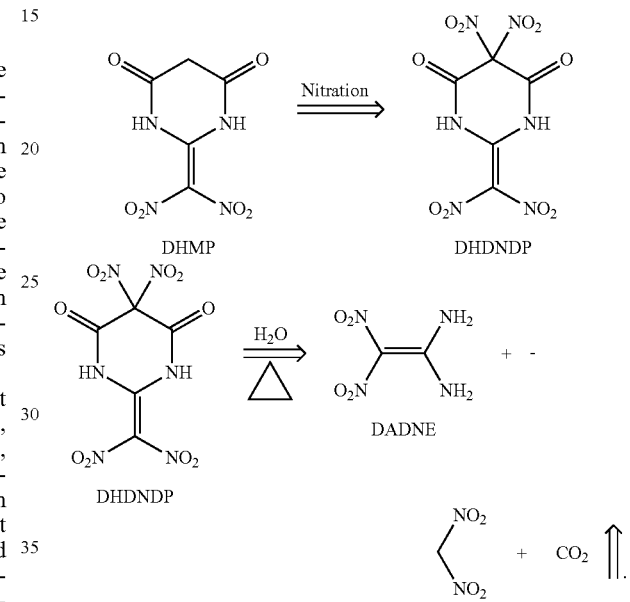

The step (1) which is to obtain DHDNDP by the nitration of DHMP is not specifically limited and any methods known in the art may be used.

The step (2) is carried out by dissolving DHDNDP prepared in the above step (1) into water in a reactor at an inner temperature of 30-60° C., and maintaining the resulted solution at the same temperature for 1.5-2.0 hours. When the temperature inside the reactor is out of said range, an eruption or sudden frothing of dinitromethane may occur, and the reaction period is needed to be lengthened to 8 hours or more.

On completion of the hydrolysis reaction in the above step (2), the step (3) is carried out by lowering the inner temperature of the reactor to 20-25° C., then filtering and washing the resulted product to obtain DADNE. The residual reaction liquid is discharged into a waste liquid tank.

Effect of the Invention

According to the present method for preparation of DADNE via the hydrolysis of DHDNDP, it is possible to avoid an eruption or sudden frothing of a reaction solution on a lab scale and even a large scale preparation as well as reduce the reaction time.

EMBODIMENTS OF THE INVENTION

Example

Hereinafter, the present invention is further illustrated in detail by way of the following examples of the present invention, which has been described with only illustrative purpose, while by no means restricting the scope of the present invention.

Example 1

Figure 1:
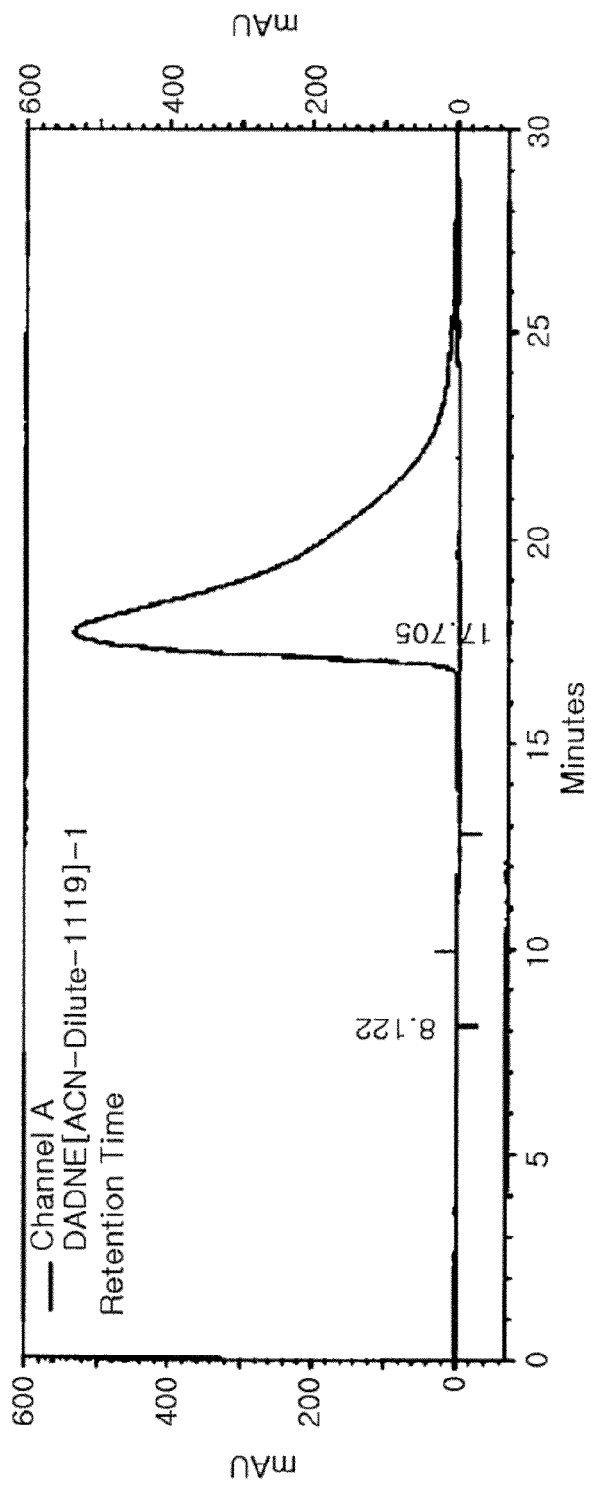
FIG. 1 is a plot showing the HPLC results of 1,1-diamino-2,2-dinitroethylene prepared according to the following example 1, showing the purity thereof.
Figure 2:
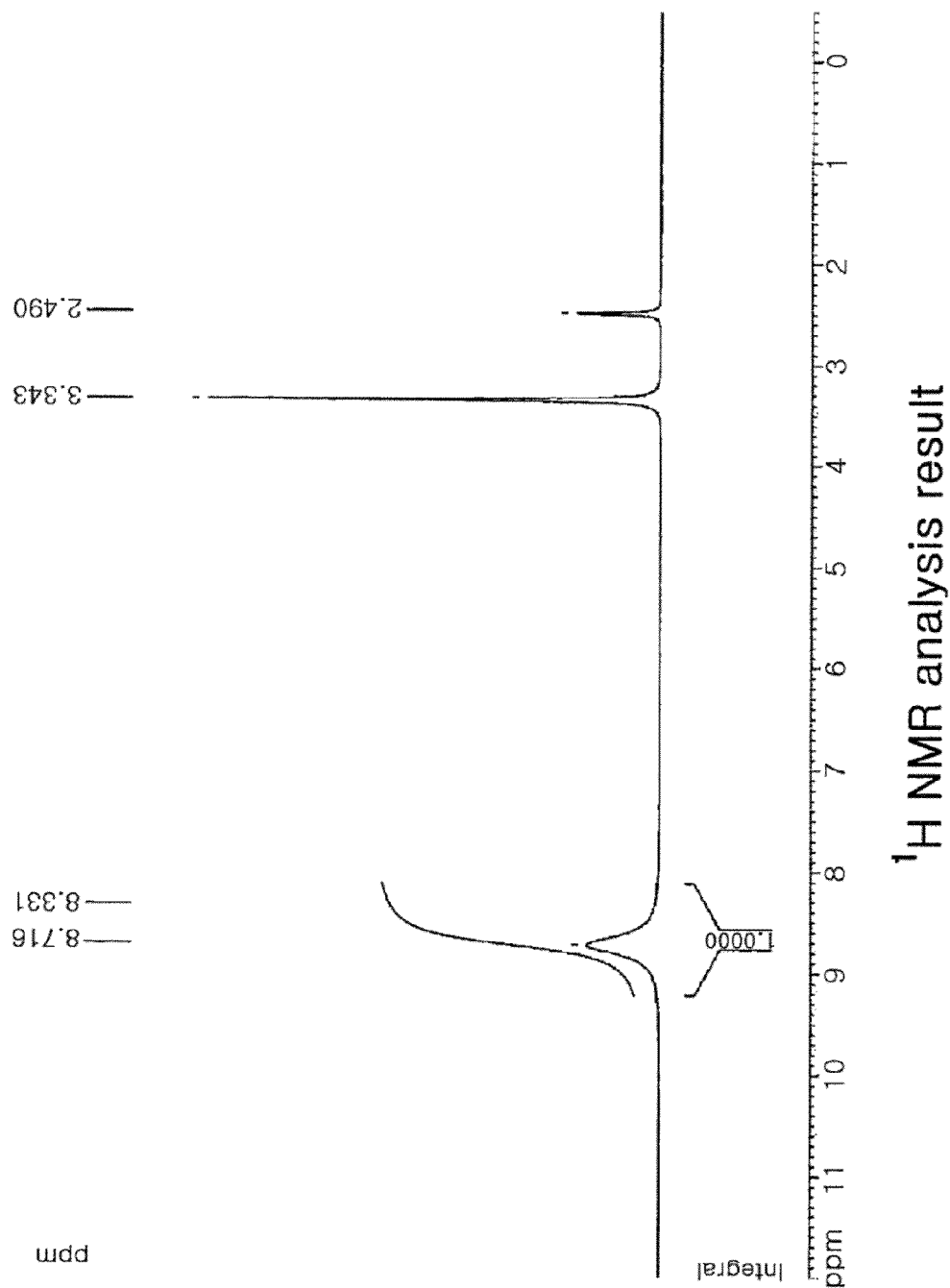
FIG. 2 is a plot showing the ¹H NMR results of 1,1-diamino-2,2-dinitroethylene prepared according to the following example 1.

A 30 L-volume reactor was charged with 6 kg of industrial water and the inside temperature was set to 50° C. While maintaining the temperature, 200 g of DHDNDP that was obtained by nitrating DHMP and filtering the resultant was fed into the reactor. The reactor was maintained at the same temperature for 2 hours, while operating the stirrer inside the reactor at 200 rpm. Then, the inside temperature of the reactor was cooled to an ambient temperature(23° C.), and the resulted product was discharged from the reactor and filtered and washed to result in 180 g of DADNE as a final product. An eruption or frothing was not observed during the reaction procedure. The filtrate resulting from the reaction was allowed to stand for a certain period in a waste water tank, maintained at 50° C., and disposed. The resulted DADNE was subjected to HPLC analysis for determining purity and ¹H NMR analysis, and the results were shown in FIG. 1 and FIG. 2.

Example 2

A 250 L-volume reactor was charged with 143 kg of industrial water and the inside temperature was set to 50° C. While maintaining the temperature, 5 kg of DHDNDP that was obtained by nitrating DHMP and filtering the resultant was fed into the reactor. The reactor was maintained at the same temperature for 2 hours, while operating the stirrer inside the reactor at 200 rpm. Then, the inside temperature of the reactor was cooled to an ambient temperature(23° C.), and the resulted product was discharged from the reactor and filtered and washed to result in 4.5 kg of DADNE as a final product. An eruption or frothing was not observed during the reaction procedure. The filtrate resulting from the reaction was allowed to stand for a certain period in a waste water tank, maintained at 50° C., and disposed.

Comparative Example

Figure 3:
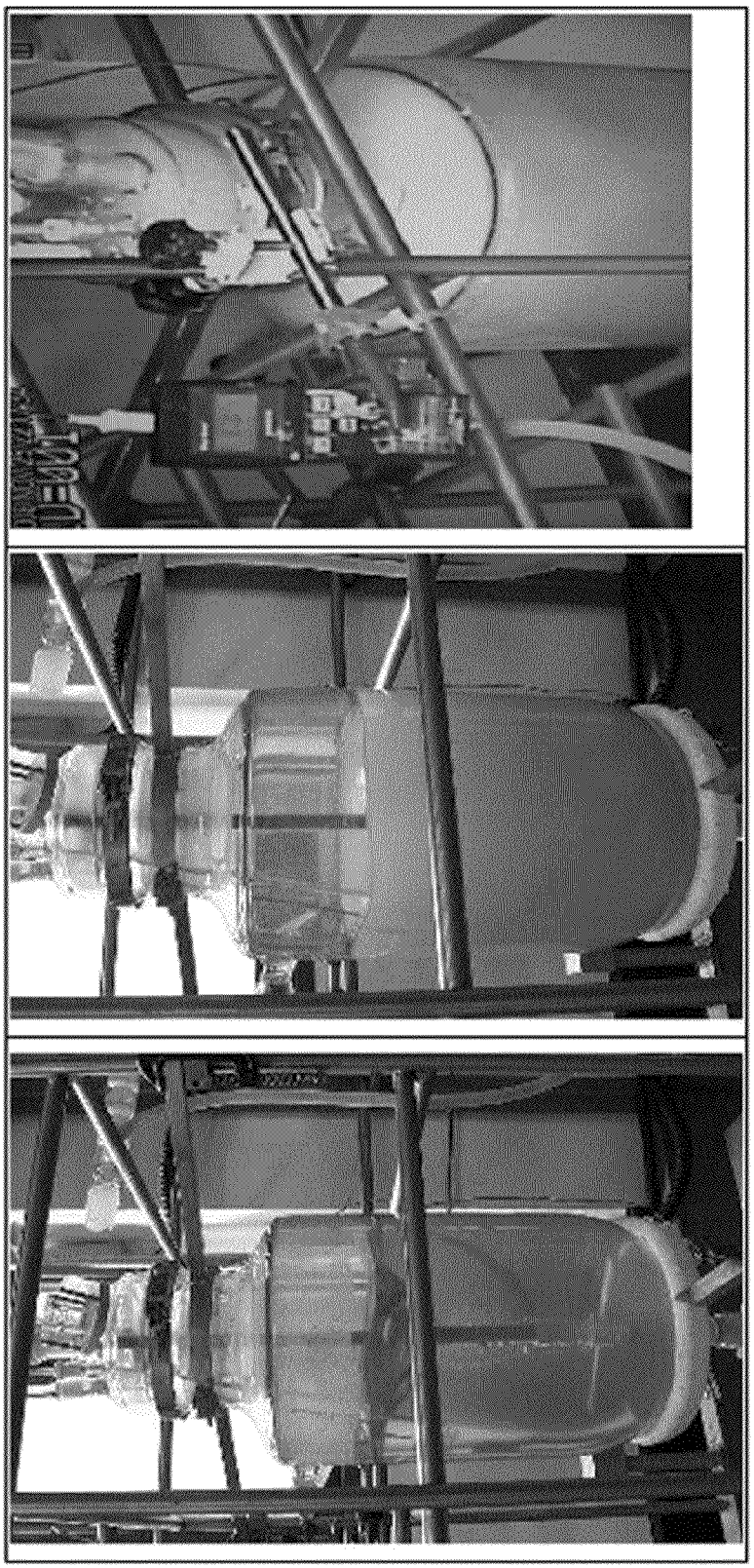
FIG. 3 is a photo showing a sudden and violent frothing occurred when the reaction is conducted according to the comparative example below.

A 20 L-volume reactor was charged with 400 equivalent amount (eq.) of water to DHDNDP and the inside temperature was set to 20° C. While maintaining the temperature, 1 eq. of DHDNDP that was obtained by nitrating DHMP and filtering the resultant was fed into the reactor. Next, the reactor was maintained at the same temperature overnight, while operating the stirrer inside the reactor at 200 rpm. Referring to FIG. 3, it was observed that a sudden and violent frothing occurred during the night. From this result, it can be found that the eruption or frothing cannot be avoided in spite of a low temperature condition, when the resulted products are maintained long in the reactor. Such eruption or frothing in the presence of the explosive final product is considered to be very dangerous.

Comparing to the results from the above Examples 1, 2 and Comparative example, although the reactants equivalent in purity and same ingredients were used in each Examples and Comparative example, the reaction time in Examples 1 or 2 was significantly shorter than that of Comparative example. Moreover, in the Examples according to the method of the present invention, regardless of the reaction scale whether it is small (Example 1) or large (Example 2), neither eruption nor sudden frothing owing to dinitromethane did not occur at all. Additionally, it is further found that the amount of water used in Examples 1 and 2 was reduced as compared to Comparative example in terms of molar ratio.

What is claimed is:

1. A method for preparation of 1,1-diamino-2,2-dinitroethylene comprising the following steps:
   (1) preparing 4,6-dihydroxy-5,5-dinitro-2-(dinitromethylene)-2,5-dihydropyrimidine through the nitration of 4,6-dihydroxy-2-methylpyrimidine;
   (2) dissolving 4,6-dihydroxy-5,5-dinitro-2-(dinitromethylene)-2,5-dihydropyrimidine prepared in the above step (1) into water in a reactor at an inner temperature of the reactor of 30-60° C., and maintaining the resultant solution at the same temperature for 1.5-2.0 hours; and
   (3) lowering the inner temperature of the reactor to 20-25° C., then filtering and washing the resultant product to obtain 1,1-diamino-2,2-dinitroethylene.

* * * * *